United States Patent [19]

Barberet-Maiolino et al.

[11] Patent Number: Plant 7,301

[45] Date of Patent: Aug. 21, 1990

[54] SPRAY CARNATION NAMED LONCHEZU

[75] Inventors: Nicole Barberet-Maiolino; Henri Blanc, both of Antibes, France

[73] Assignee: Laboratoire de Physiologie Vegetale, La Londe-les-Maures, France

[21] Appl. No.: 266,130

[22] Filed: Oct. 11, 1988

[51] Int. Cl.[5] ..... A01H 5/00

[52] U.S. Cl. ..... Plt./70

[58] Field of Search ..... Plt./70, 71

*Primary Examiner*—James R. Feyrer

*Attorney, Agent, or Firm*—Charles W. Rummler

[57] ABSTRACT

A new spray carnation cultivar particularly distinguished by its relatively small, primrose yellow flowers having clean, unblemished petals regularly imbricated to provide a pleasing, well formed flower, which is produced profusely during the Spring, midseason and Fall blooming periods on a strong, vigorous plant having an average height of about 105 cm. and which has abundant foliage and good resistance to *Fusarium oxysporum.*

1 Drawing Sheet

BACKGROUND OF THE NEW PLANT

This new spray carnation plant originated as a seedling of a hybrid developed by us at our nursery at 83250 La Londe-Les-Maures, France, by our crossing two selected carnation varieties from our collection maintained for breeding purposes at our nursery at La Londe, the selected breeding varieties being unnamed and unpatented. This particular seedling of the said hybrid was chosen for propagation because of its clear, bright yellow flowers which the plant produced profusely with a vigorous, upright growth habit. This selected seedling was propagated from cuttings under our direction at La Londe with very satisfactory results, which prompted us to direct continued propagation at our nursery through several successive generations both by cuttings and by in vitro propagation procedures, thereby establishing that the distinctive features of the new plant would be retained from generation to generation and assuring its homogeneity. Present propagation of this new plant is being done at 83250 La Londe-Les-Maures, France.

DESCRIPTION OF THE DRAWING

This new carnation cultivar is illustrated by the accompanying photographic drawing, which shows stems of the new variety with buds and blooms in several stages of development, the colors shown being as close to those herein specified as is reasonably possible to obtain by conventional, professional photographic procedures.

DESCRIPTION OF THE NEW PLANT

The following is a detailed description of our new spray carnation cultivar based upon our observations during the Spring of the current year of plants grown in southern France, the color designations being according to The R.H.S. Colour Chart published by The Royal Horticultural Society of London, England.

THE PLANT

Origin: Seedling.

Parentage:

*Seed parent.*—Variety 80 MB 19.

*Pollen parent.*—Variety 80 MFV 1. Both varieties are identified in breeding records maintained at our nursery at La Londe.

Classification:

*Botanic.*—*Dianthus caryophyllus.*

*Commercial.*—Spray Carnation.

Form: An erect bush comprising at least four stems emitted near the ground.

Height: Averages about 105 cm.

Main stem length: Less than about 15 cm. due to pinching.

Branching character: The plant is well branched.

Growth: Vigorous, upright and rigid.

Foliage:

*Quantity.*—Moderately abundant.

*Number of leaves.*—More than 120.

*Leaf size.*—About 12.5 cm. long and 0.8 cm. wide at the seventh node.

*Leaf shape.*—Oblong with entire and curved margin.

*Texture.*—Leathery.

*Ribs and veins.*—Hardly noticeable.

*Rachis.*—Hardly noticeable.

*Color.*—Both upper and under sides, 189-A.

THE BUD

Size: Small.

*Diameter.*—Averages about 1.3 cm.

*Length.*—Averages about 2.3 cm.

Form: Long cylindrical.

Rate of opening: Normal.

Color of petals: When sepals first divide, Light Yellow 4-B. When petals begin to unfurl, 4-B.

Sepals:

*Number.*—Five or six.

*Shape.*—Generally ovoid but joined together at their lower parts and having an acuminate tip.

*Character.*—Hooded over the bud and upstanding when the flowers open.

*Color.*—Inside, 148-D. Outside, 144-C and 138-B.

*Striae.*—Longitudinal.

Calyx:

*Shape.*—Cylindrical and long.

*Splitting.*—The calyx does not split.

*Appearance.*—Smooth.

Flower Stem:

*Character.*—Erect and rigid.
*Color.*—189-A.

THE FLOWER

Blooming habit: Recurrent and profusely during Spring, midseason and Fall blooming periods.
Size of flower: Small.
*Diameter.*—Averages about 5.6 cm.
*Depth.*—Averages about 4.2 cm.
Borne: Singly on an individual stem of a cluster.
Shape: When bloom first opens, high-centered. When bloom matures, dome-shaped.
Petalage:
*Number of petals.*—About forty-seven, in average.
*Arrangement.*—Imbricated.
*Form.*—Fan-shaped with rounded edges and a very little serration at the apex.
*Texture.*—Leathery.
*Aspect.*—Satiny.
*Color.*—Outer petals: Body — Primrose Yellow 4-B. Base — Greenish white. Reverse side — 4-B. Inside petals: The same as the outer petals.
*Petaloids.*—Number: Less than six. Size: Smaller than the petals. Color: The same as the petals.
Flower stem:
*Length.*—Averages about 68.5 cm. when cut at the tenth node.
*Color.*—189-A.
*Character.*—Upright with good strength.
Discoloration after full bloom: Very little.
Fragrance: Perceptible.
Persistence: The flowers hang on and dry.
Disease resistance: Resistant to *Fusarium oxysporum* as observed I.N.R.A. 06600 Antibes, France.
Lasting quality: At least ten days as a cut flower in vase keeping.

REPRODUCTIVE ORGANS

Stamens:
*Number.*—About twelve to eighteen.
*Arrangement.*—Encircling the ovary.
*Anthers.*—Size: About 4 mm. Color: Whitish.
*Filaments.*—Length: Averages about 1.6 cm. Color: Whitish.
Pistils:
*Number.*—Two or three.
*Styles.*—Length: About 2.9 cm. Color: Yellowish.
*Stigma.*—Color: Yellowish.
Characteristics of ovaries: Ribbed.

The present variety most nearly resembles the variety 'Londragel' (U.S. Plant Pat. No. 6,571) but differs materially by having a longer stem and its flowers never show red markings.

The characteristics of the above described variety may be more-or-less modulated when grown under various environmental conditions, such as the nature of the ground, method of cultivation and latitude, as observed of plants grown in Spring in southern France.

We claim:

1. The new and distinctive spray carnation plant substantially as herein shown and described, characterized by the clean, bright yellow color of its blooms, its profuse production of blooms, its relatively long flower stems, its good production of foliage and its vigorous, upright growth habit.

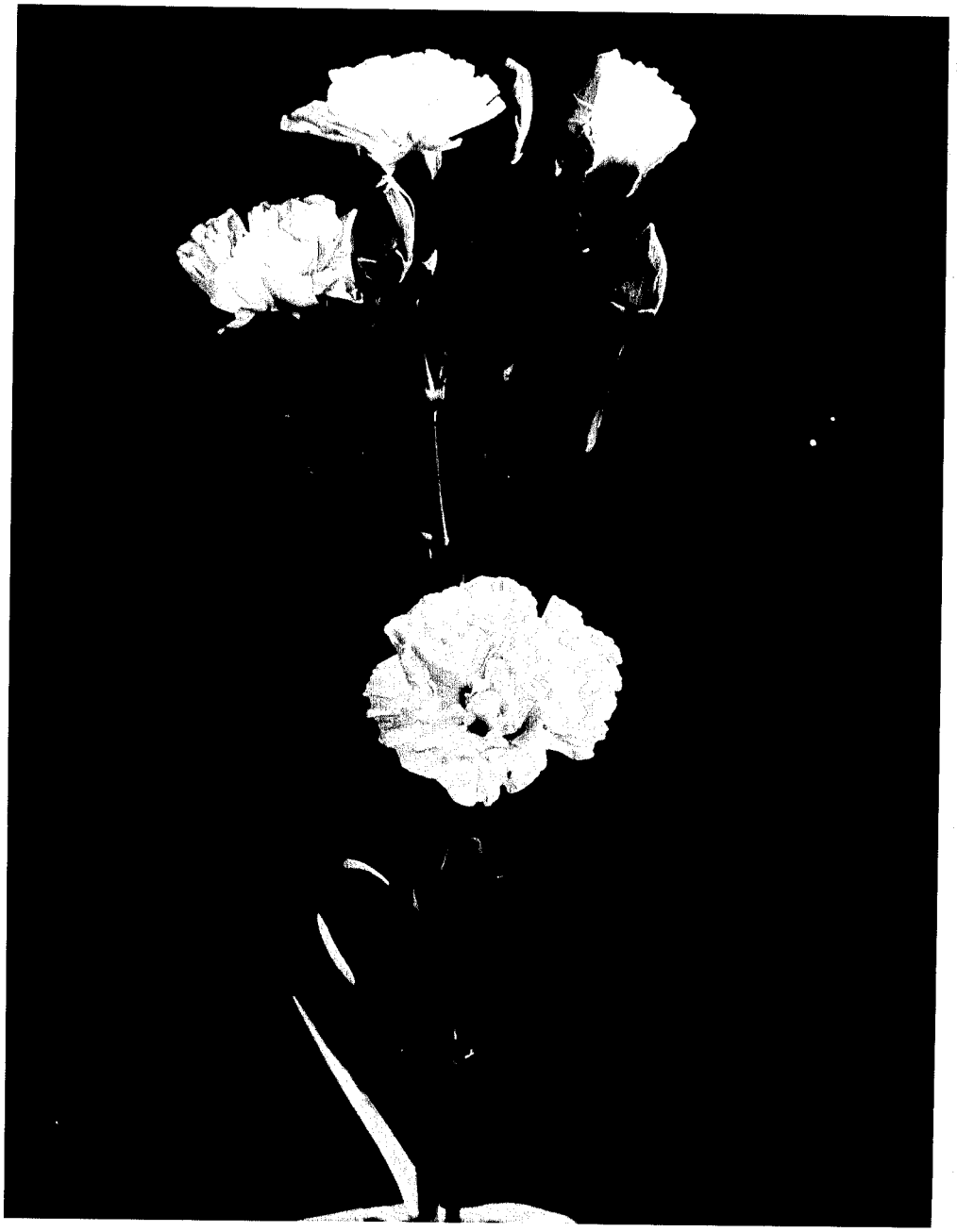

* * * * *